United States Patent
Vogel

(10) Patent No.: US 10,130,281 B2
(45) Date of Patent: Nov. 20, 2018

(54) DEVICE FOR MEASURING BIOIMPEDANCES

(75) Inventor: Sönke Vogel, Hamburg (DE)

(73) Assignee: SECA AG, Reinach BL (CH)

( * ) Notice: Subject to any disclaimer, the term of this patent is extended or adjusted under 35 U.S.C. 154(b) by 21 days.

(21) Appl. No.: 13/700,803

(22) PCT Filed: Mar. 14, 2011

(86) PCT No.: PCT/DE2011/000262
§ 371 (c)(1),
(2), (4) Date: Nov. 29, 2012

(87) PCT Pub. No.: WO2011/150903
PCT Pub. Date: Dec. 8, 2011

(65) Prior Publication Data
US 2013/0072813 A1   Mar. 21, 2013

(30) Foreign Application Priority Data
Jun. 1, 2010  (DE) .......... 10 2010 023 122

(51) Int. Cl.
*A61B 5/053* (2006.01)
*A61B 5/00* (2006.01)
*G01G 19/50* (2006.01)

(52) U.S. Cl.
CPC .......... *A61B 5/0537* (2013.01); *A61B 5/4872* (2013.01); *A61B 5/6887* (2013.01); *G01G 19/50* (2013.01)

(58) Field of Classification Search
CPC .............................. A61B 5/0537; A61B 5/053
USPC ....................................................... 600/547
See application file for complete search history.

(56) References Cited

U.S. PATENT DOCUMENTS

| | | | |
|---|---|---|---|
| 6,155,994 A * | 12/2000 | Hubbard et al. | 601/5 |
| 6,165,129 A | 12/2000 | Bates | |
| 6,256,532 B1 | 7/2001 | Cha | |
| 6,327,494 B1 | 12/2001 | Sakai | |
| 7,892,158 B2 * | 2/2011 | Varga | A63B 21/4017 482/141 |
| 2008/0287816 A1* | 11/2008 | Honda | 600/508 |
| 2011/0147094 A1* | 6/2011 | Gerster | 177/4 |

FOREIGN PATENT DOCUMENTS

| | | |
|---|---|---|
| DE | 102006038399 A | 2/2008 |
| EP | 0998875 X | 5/2000 |
| JP | 2003265429 X | 9/2003 |
| JP | 2006175247 A | 7/2006 |
| WO | WO 2008019637 A1 * | 2/2008 ............. A61B 5/053 |

OTHER PUBLICATIONS

English Translation of JP 2003265429.*

* cited by examiner

*Primary Examiner* — Daniel L Cerioni
*Assistant Examiner* — Yasmeen S Warsi
(74) *Attorney, Agent, or Firm* — Lucas & Mercanti, LLP; Klaus P. Stoffel

(57) ABSTRACT

The device is used to measure bioimpedances and has in each case at least one measurement electrode for each foot and each hand of a person who is to be measured. The electrodes are connected to an evaluation unit. In addition, at least one balance is used to determine a body weight of the person who is to be measured. The hand electrodes, provided for contact with the hands of the person who is to be measured, are arranged in the area of at least one positionable support element.

8 Claims, 4 Drawing Sheets

DEVICE FOR MEASURING BIOIMPEDANCES

The present application is a 371 of International application PCT/DE2011/000262, filed Mar. 14, 2011, which claims priority of DE 10 2010 023 122.3, filed Jun. 1, 2010, the priority of these applications is hereby claimed and these applications are incorporated herein by reference.

BACKGROUND OF THE INVENTION

The invention pertains to a device for measuring bioimpedances, which comprises at least one measuring electrode for each foot and each hand of the person being measured, in which the electrodes are connected to an evaluation device, and in which at least one scale is provided for determining the body weight of the person being measured.

These types of devices are typically used to determine the relative amount of fat in human tissue. Because of the relatively low percentage of water in fatty tissue, the electrical resistance of such fatty tissue is much greater than the electrical resistance of muscles or of body fluids. Through an appropriate measurement of the resistance or impedance in combination with a weight measurement, it is therefore possible to determine the percentage of fat.

To obtain accurate measurements, it is essential for the measuring current to flow through at least most of the body. For accurate measurements, therefore, electrodes are required both in the area of the feet and in the area of the hands.

So that the measurement can be carried out quickly and in a manner comfortable for the user, it is necessary for the contact with the electrodes to be established easily and comfortably. The idea is therefore for the person being measured to stand with each foot on one of the associated electrodes and to grip the electrodes provided for the hands. Establishing good contact between the feet and the foot electrodes is relatively easy if the person being measured can see immediately how he is supposed to orient himself. Correct contact with the hand electrodes to be gripped depends on the correct relative positioning between the hands the electrodes.

SUMMARY OF THE INVENTION

The goal of the present invention is to design a device of the type described above in such a way that correct positioning of the electrodes relative to the person to be measured is facilitated.

This goal is achieved according to the invention in that the electrodes provided for contact with the hands of the person to be measured are arranged in the area of at least one positionable support element.

Arranging the electrodes in the area of a positionable support element offers several advantages. First, it is possible to adapt the positioning of the electrodes to the height of the user, to his specific anatomy, and to his posture. This adaptability leads to good electrical contact between the electrodes and the hands of the user, but it also makes it easier for the user to adopt a comfortable stance. The use of the support element also makes it possible to facilitate the correct positioning of the user relative to the scale and also to the foot electrodes. This, too, helps to obtain to a correct measurement.

The device can be adapted to the height of the user by designing the support element so that its height can be adjusted.

A stance with spread-out arms is facilitated by designing the support element so that it can be positioned with a horizontal directional component.

Obtaining a comfortable gripping position and/or making the necessary adjustment is facilitated by designing the support element so that it can be rotated.

Predetermined positioning paths can be defined by designing the support element so that it can slide along a guide element.

A sturdy mechanical design is obtained by attaching the guide element to a vertical column, which carries an indicator.

The mechanical strength of the device can also be increased by using struts to brace the ends of the guide element facing away from the vertical column.

According to one embodiment, it is provided that the guide element is designed so that its height can be positioned relative to the vertical column.

The device becomes especially easy to use when the ends of the guide element facing away from the vertical column are lower in a vertical direction than the area of the guide element facing the vertical column.

An effective support function for the user and at the same time optimal conditions for adjusting the electrodes are achieved by giving the guide element a semicircular shape.

Especially accurate measurement results are obtained by designing the evaluation device both to evaluate a measured alternating current and to evaluate a measured alternating voltage.

The positionability of the at least one support element for the electrodes defined above can be realized in various ways. According to a first design variant, a support element is provided for each of the electrodes assigned to the user's hands, this support element being designed so that its position can be varied either along the guide element or together with the guide element. The position of the support element is changed as appropriate to ensure that the electrodes assume their optimal positions.

According to another design variant, at least two support elements for the electrodes are provided for each hand of the user, wherein the support elements are arranged without the ability to move relative to the guide element. For example, three support elements, each of these preferably for two electrodes, are arranged along the length of the guide element. The user grips the electrodes which are in the most favorable position in relation to his anatomy. Gripping the electrodes in this way as a function of the specific anatomy of the user is facilitated in particular by designing the guide element so that it extends downward at a slant and/or curves downward from the vertical column.

With respect to the angle of the guide element relative to the horizontal, a range of 10-40° has been found advisable for the angle in question. A range of 20-30° is preferred. In the case of the present exemplary embodiment, an angle of approximately 25° is used.

Exemplary embodiments of the invention are illustrated schematically in the drawings:

DETAILED DESCRIPTION OF THE INVENTION

Figure 1:
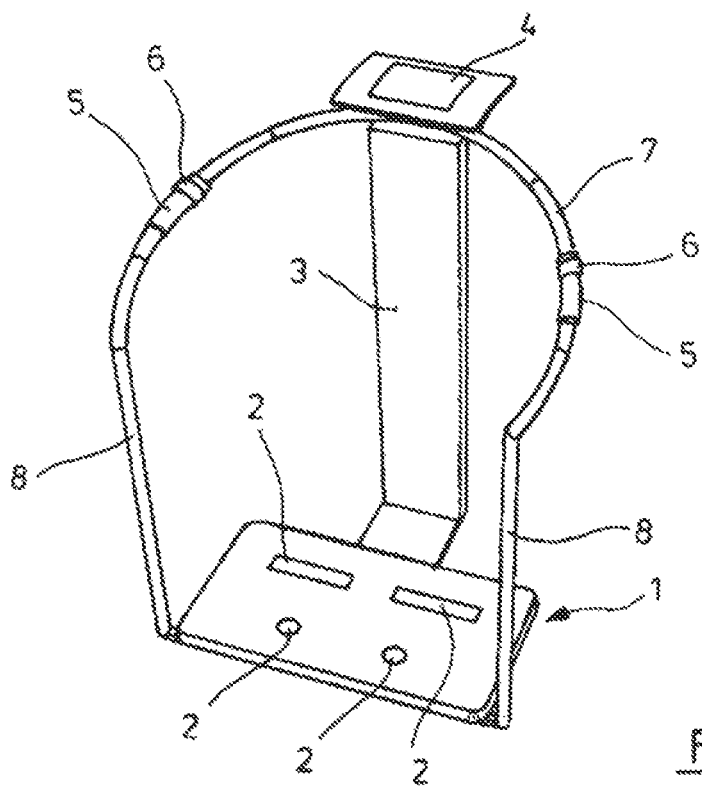
FIG. 1 shows a perspective view of a device with a railing-like guide element for the hand electrodes and with foot electrodes, arranged in the area of a scale.

According to the embodiment in FIG. 1, the device for measuring bioimpedances comprises a scale 1, which is provided with foot electrodes 2. In the exemplary embodiment shown here, two foot electrodes 2 are provided for each foot of the person to be measured.

An indicator 4 is arranged in the area of a vertical column 3. The indicator 4 can be designed as a display screen. Operating elements can also be provided in the area of the vertical column 3. The indicator 4 is arranged at a convenient reading height for the user.

Figure 4:
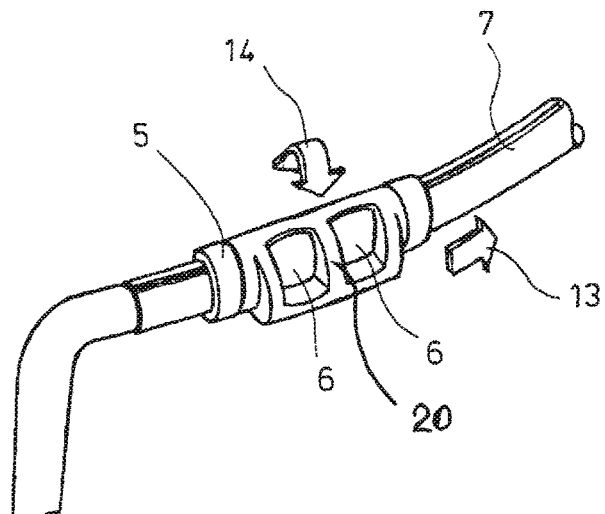
FIG. 4 shows a schematic diagram illustrating the ability of the support element for the electrodes both to turn and to shift laterally relative to a guide element.

Hand electrodes 6 are arranged in the area of support elements 5. Two hand electrodes 6 are preferably used for each hand of the user. As seen in FIG. 4, the hand electrodes are separated by a web 20. The web 20 projects above the contact surfaces of the hand electrodes 6.

The support elements 5 are designed so that they can be positioned along a guide element 7. In the exemplary embodiment shown here, the guide element 7 is attached to the vertical column 6 and comprises a semicircular shape. FIG. 1 shows an embodiment in which the ends of the guide element 7 facing away from the vertical column 3 are supported by struts 8 relative to a surface for standing. The ends of the guide element 7 arranged in the area of the struts 8 are preferably positioned on a level lower than that of the area of the guide element 7 connected to the vertical column 3. The guide element 7 and/or the struts 8 can be produced out of tubular material. FIG. 1 shows a railing-like configuration of the wide element 7.

Figure 2:
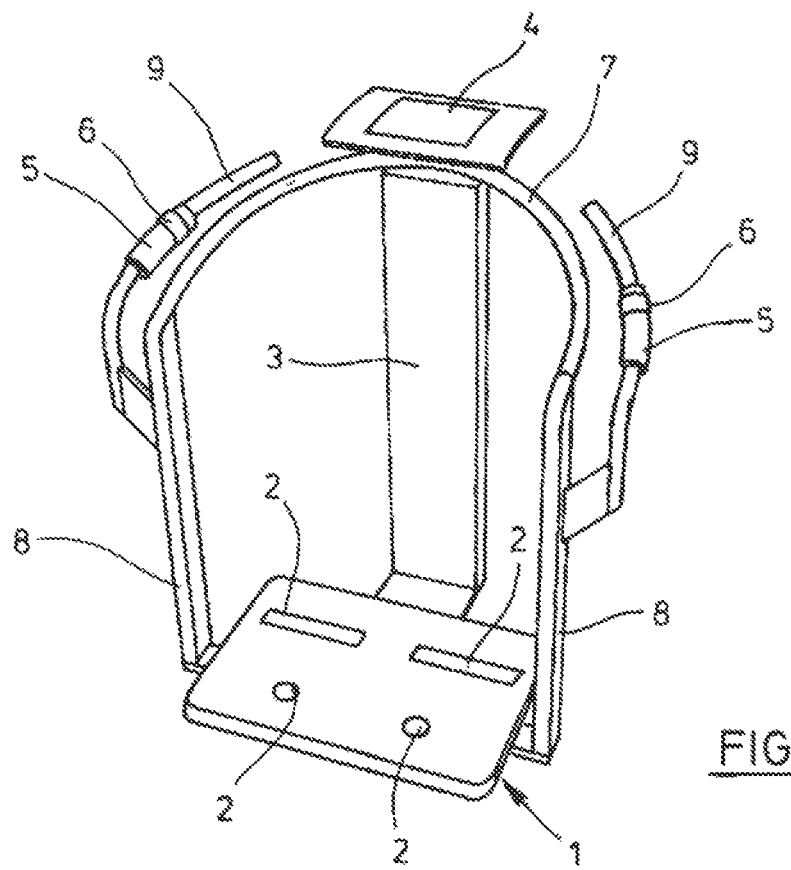
FIG. 2 shows an embodiment representing a modification of the one shown in FIG. 1 with the addition of lateral support arms for the electrodes.

FIG. 2 shows a modification of the embodiment according to FIG. 1. In contrast to FIG. 1, in which the struts 8 are positioned at the sides of the scale 1 adjacent to the forward edge of the scale 1, i.e., the edge facing away from the vertical column 3, in FIG. 2 the struts are located more toward the center of the two sides of the scale 1. In addition, the support elements 5, in contrast to FIG. 1, are arranged in the area of additional lateral support arms 9 of the guide element 7. The area of the guide element 7 analogous to that of the embodiment according to FIG. 1 serves here, in the embodiment in FIG. 2, only as support for the user, and it also helps the user to adopt the correct physical orientation.

Figure 3:
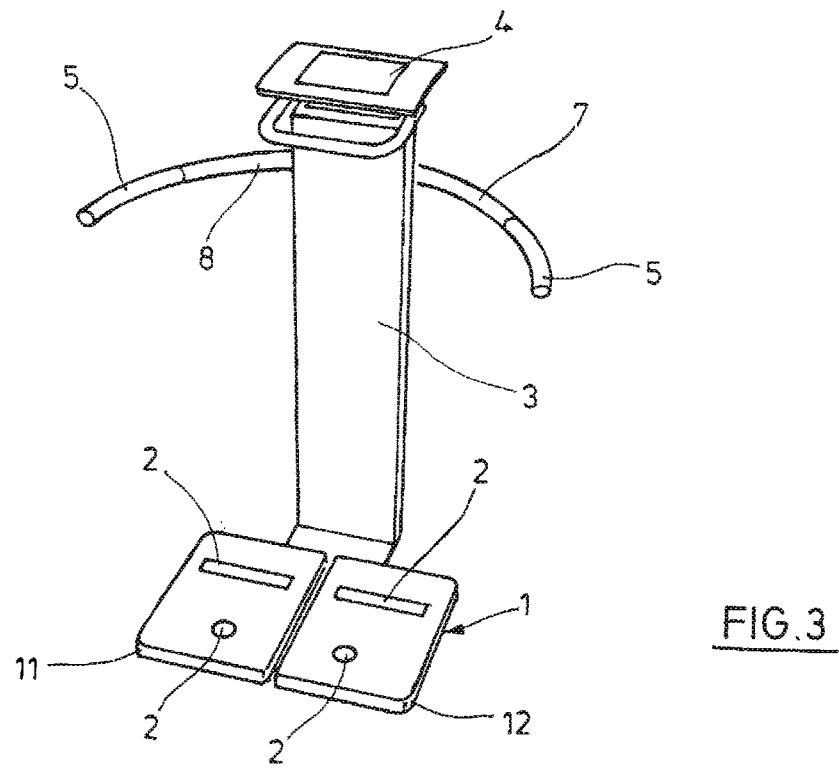
FIG. 3 shows an embodiment representing a modification of the one shown in FIG. 1 with shortened guide elements for the electrodes.

According to the embodiment in FIG. 3, the guide element 7 consists only of two arms projecting laterally from the vertical column 3. To increase the reliability with which the device can be used, an additional handle 10 is used. The scale 1 is divided into two segments 11, 12.

FIG. 4 illustrates a possibility for positioning the support element 5 relative to the guide element 7. The support element 5 is positionable both in a lengthwise direction 13 and in a circumferential direction 14 of the guide element 7. As a result, the optimal positioning can be achieved for the specific anatomy of the user.

Figure 5:
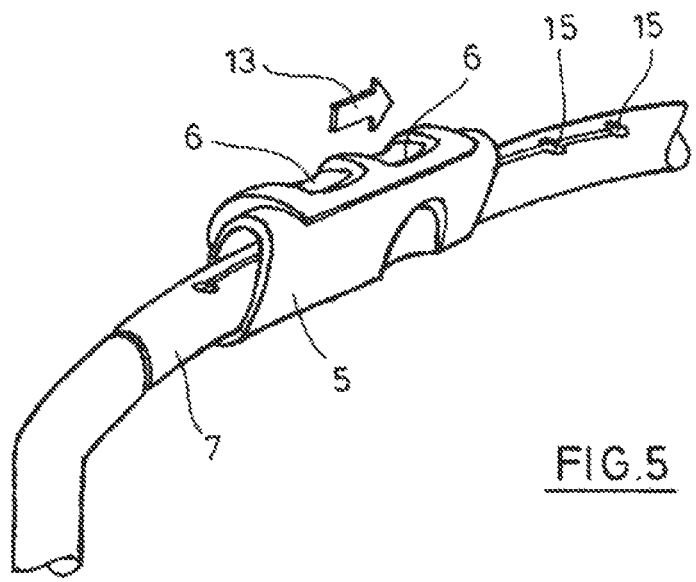
FIG. 5 shows another diagram illustrating the positionability of the support element for the electrodes.

According to the embodiment in FIG. 5, latch points 15 for the support element 5 are provided in the area of the guide element 7. The latch points 15 provide defined positionings for the support element 5 and make it easier to ensure that the hand electrodes 6 are positioned in the same way relative to the vertical column 3.

Figure 6:
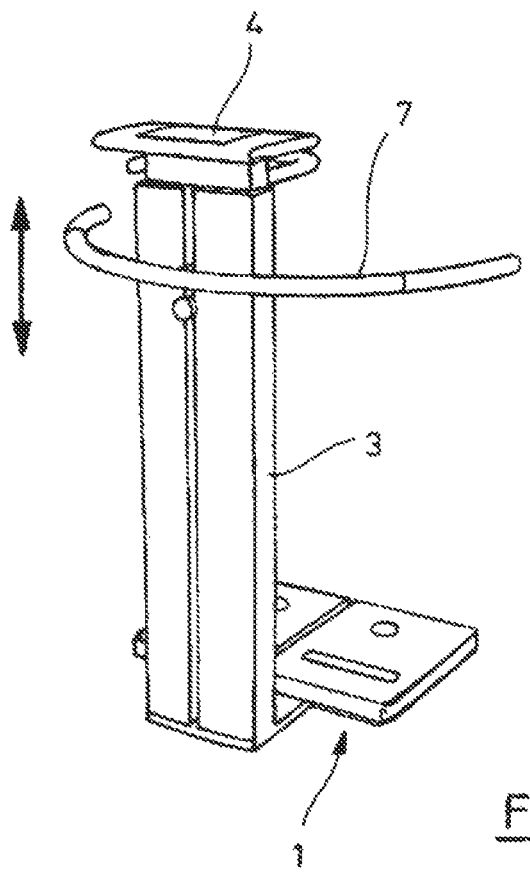
FIG. 6 shows a perspective view illustrating the adjustability of the height of the support element.

In an embodiment similar to that of FIG. 3, FIG. 6 illustrates how the height of the guide element 7 is adjusted relative to the vertical column 3.

Figure 7:
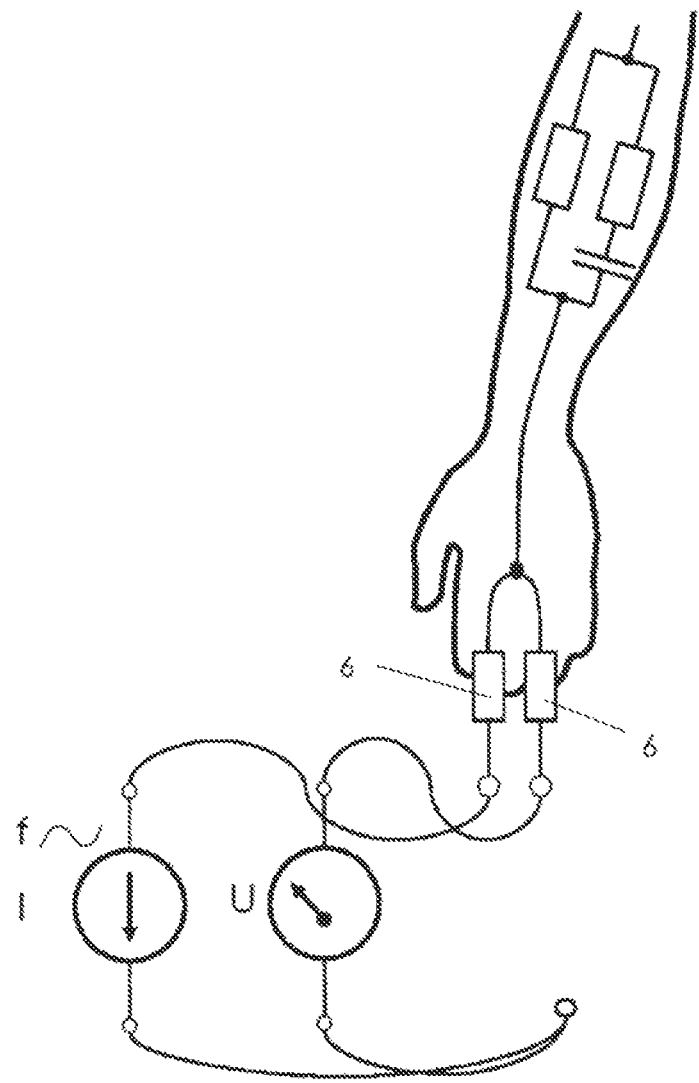
FIG. 7 shows a schematic diagram illustrating the principle of the measurement.

FIG. 7 illustrates the measurement principle. An alternating voltage is applied to the hand electrodes 6, and both the resulting alternating current and the alternating voltage at the hand electrodes 6 are determined. Providing separate measurement pathways for the alternating current and the alternating voltage in this way avoids the falsification of the measurement result caused by the impedance of the skin in the contact area of the hand electrodes 6.

Through the arrangement of the support element 5 in the area of the guide element 7 and through the design of the guide element 7, the person to be measured will always assume a position in which the arms are spread slightly out to the side. This prevents the arms from contacting the side of the user's body, which would falsify the measurement result through the creation of additional paths of electrical conductivity. The previously described design of the guide element 7 in the manner of a hand railing and the slant of the course of the guide element 7 relative to the horizontal plane have proven to be advantageous in encouraging this lateral spreading of the arms. Regardless of the user's actual height and arm length, the user will be able to place his hands in a position which is optimal for the performance of the measurement.

The invention claimed is:

1. A device for measuring bioimpedances, comprising at least two measuring foot electrodes for each foot and at least two measuring hand electrodes for each hand of a person to be measured; an evaluation device, the at least two measuring foot electrodes and the at least two measuring hand electrodes being connected to the evaluation device; at least one scale for determining body weight of the person being measured; at least four positionable electrode support elements, wherein the at least two measuring hand electrodes provided for contact with the hands of the person being measured are arranged in an area of each of the at least four positionable electrode support elements; and a guide element, wherein the at least four electrode support elements include at least two electrode support elements provided for each hand of the person at different positions along the guide element to facilitate differing arm lengths of people being measured, each of the at least two electrode support elements having two measuring hand electrodes, wherein the at least two electrode support elements are positionable with a horizontal directional component, wherein the at least two electrode support elements are rotatable about a longitudinal axis of the guide element, wherein the at least two electrode support elements each have a length and each of the at least two electrode support elements is mounted on the guide element so that the entire length of each of the at least two electrode support elements is slidable along the guide element in a direction of said longitudinal axis of the guide element, wherein each of the electrode support elements has a contour curved about a longitudinal axis of the electrode support element in a gripping direction of a user, wherein the at least two measuring hand electrodes on each electrode support element are separated by a central web so as to increase grasping security, wherein the central web projects perpendicular to the longitudinal axis of the guide element and above contact surfaces of the at least two measuring hand electrodes.

2. The device according to claim 1, wherein the at least two electrode support elements are configured so as to be height adjustable.

3. The device according to claim 1, and further comprising a vertical column that carries an indicator, the guide element being attached to the vertical column.

4. The device according to claim 3, wherein the guide element has ends facing away from the vertical column, and further comprising struts that support the ends of the guide element.

5. The device according to claim 3, wherein the guide element is height adjustable relative to the vertical column.

6. The device according to claim 4, wherein the ends of the guide element facing away from the vertical column are lower in a vertical direction than an area of the guide element facing the vertical column.

7. The device according to claim 1, wherein the guide element has a semicircular shape.

8. The device according to claim 1, wherein the evaluation device is operative to evaluate both a measured alternating current and a measured alternating voltage.

* * * * *